(12) United States Patent
Wu (10) Patent No.: US 10,244,992 B2
(45) Date of Patent: Apr. 2, 2019

(54) INTERFACE FOR POSITRON EMISSION TOMOGRAPHY (PET) SCANNER DETECTOR MODULE

(71) Applicant: Yibao Wu, Cypress, CA (US)

(72) Inventor: Yibao Wu, Cypress, CA (US)

( * ) Notice: Subject to any disclaimer, the term of this patent is extended or adjusted under 35 U.S.C. 154(b) by 0 days.

(21) Appl. No.: 16/150,257

(22) Filed: Oct. 2, 2018

(65) Prior Publication Data

US 2019/0029613 A1    Jan. 31, 2019

Related U.S. Application Data

(63) Continuation-in-part of application No. 15/363,165, filed on Nov. 29, 2016, now abandoned.

(60) Provisional application No. 62/348,048, filed on Jun. 9, 2016.

(51) Int. Cl.
*A61B 6/00* (2006.01)
*A61B 6/03* (2006.01)
*G01T 1/29* (2006.01)

(52) U.S. Cl.
CPC ............. *A61B 6/037* (2013.01); *A61B 6/56* (2013.01); *G01T 1/2985* (2013.01); *A61B 6/4258* (2013.01)

(58) Field of Classification Search
CPC ............................. A61B 6/037; G01T 1/2985
See application file for complete search history.

(56) References Cited

U.S. PATENT DOCUMENTS 9,596,073 B1 * 3/2017 Reyes .................. H04L 7/0037

* cited by examiner

*Primary Examiner* — Edwin C Gunberg
(74) *Attorney, Agent, or Firm* — Che-Yang Chen; Law Offices of Scott Warmuth (57) ABSTRACT

An integrated interface of a detector module of a Positron Emission Tomography (PET) may include a power module, a clock module, a synchronization module, and a communication module. In one embodiment, Gigabit Ethernet, 10G Ethernet, Fast Ethernet (100M), 10M Ethernet or custom speed Ethernet based solution can be used in the communication module. In the power module, the power is can be transmitted by standard PoE (Power over Ethernet) method, while the clock can be recovered from Ethernet in the clock module. In the synchronization module, in one embodiment, the synchronization can be done through a dedicated package and/or IEEE1588. The integrated interface can be implemented in other systems. For example, it can be used in a gamma camera system or gamma probe, especially a dynamic gamma camera or handheld gamma camera.

12 Claims, 9 Drawing Sheets

FIG. 9 ly used in nuclear medicine and pre-clinical research, which produces a static or dynamic three-dimensional image or parameters of functional biological processes in live bodies. It can be used in cancer detection, staging and restaging, treatment planning and monitoring, as well as drug development. During a PET scan, a patient is introduced with positron-emitting radionuclide, which produces pairs of photons, the PET system then detects the photons and reconstructs the three-dimensional images or parameters showing the biological process inside the patient body.

INTERFACE FOR POSITRON EMISSION TOMOGRAPHY (PET) SCANNER DETECTOR MODULE

CROSS-REFERENCE OF RELATED APPLICATIONS

The present invention is a continuation-in-part (CIP) application of Ser. No. 15/363,165 filed on Nov. 29, 2016 now pending, which claims priority under 35 U.S.C. § 119 (e) to U.S. Provisional Patent Application Ser. No. 62/348,048, filed on Jun. 9, 2016, the entire contents of which are hereby incorporated by reference.

FIELD OF THE INVENTION

The present invention relates to a positron emission tomography (PET) detector module, and more particularly to a PET detector module having an integrated interface with power, clock, synchronization, and communication.

BACKGROUND OF THE INVENTION

Positron emission tomography (PET) is a functional imaging technique widely used in nuclear medicine and pre-clinical research, which produces a static or dynamic three-dimensional image or parameters of functional biological processes in live bodies. It can be used in cancer detection, staging and restaging, treatment planning and monitoring, as well as drug development. During a PET scan, a patient is introduced with positron-emitting radionuclide, which produces pairs of photons, the PET system then detects the photons and reconstructs the three-dimensional images or parameters showing the biological process inside the patient body.

To build a PET system, detector modules are developed to detect the photon pairs, which usually include high-density scintillator with photodetectors or directly gamma ray detectors to detect each individual photon with precise location, energy and time information, as well as with high efficiency. All detected events are sent to a centralized coincidence processing unit or distributed processing units, or software to sort out the prompt coincident events and/or the random coincident events.

The detector module may include power, clock, synchronization, and communication sections to work together but they are separately built. Conventionally, there are four different kinds of connectors and each kind is responsible for only one function.

Due to limited scan time, injection dose and the demand of high image quality, various methods are proposed to increase the system sensitivity. High-density detector or multiple detectors can improve the system sensitivity, and to further improve the image quality.

Recently, "Time of Flight" (TOF) is introduced and proven to improve the imaging quality and/or reduce injection dose and/or scan time. Without TOF, each detected event is back projected along a line (called line of response or LOR) within the range of object being imaged. With TOF, this range can be reduced by locating the event within the distance traveled, which is half of the product of the TOF and speed of light. For a non-TOF system, the required timing resolution is be typically below 5 nanoseconds, while a TOF system needs the timing resolution to be typically below 1 nanosecond, which requires the clock alignment (along with sync) to be below 1 nanosecond, or even less, such as around hundreds of picoseconds, as described in "Update on time-of-flight PET imaging" by Suleman Surti published on Journal of Nuclear Medicine. To achieve good timing or TOF, a precision clock and synchronization is needed in addition to the power and communication. However, these four components are still separately built, which causes inconveniences to the users.

There is a need for an integrated interface for the detector module including all components in a cost effective way. A unified integrated interface can be used to simplify the module design and the coincidence processing unit or uplink.

SUMMARY OF THE INVENTION

In one aspect, an integrated interface of a detector module of a Positron Emission Tomography (PET) may include a power module, a clock module, a synchronization module, and a communication module. In one embodiment, Gigabit Ethernet, 10G Ethernet, Fast Ethernet (100M), 10M Ethernet or custom speed Ethernet based solution can be used in the communication module. The communication module may further include at least one PC connected to CPU to process the data received from the detector.

For the power module, a power module may supply power to a detector using a cable, from a coincidence processing unit (CPU) or a separate source. In one embodiment, the power can be transmitted by a standard PoE (Power over Ethernet), which is configured to pass electric power along with data on twisted pair Ethernet cabling, and allows a single cable to provide both data connection and electric power to devices. It is noted that the power is delivered over the cable with a standard procedure to make sure the power delivery is safe. For example, only a small amount of power is configured to be delivered at the beginning.

For the clock module, it is proved that the clock can be recovered from Ethernet. In one embodiment, the clock module has a recovery circuit to get the clock from the serial data, and the recovered clock is used to send the data back. A circuitry on the coincidence processing unit or uplink can be used to recover the clock from the detector module, monitor the difference with a Time to Digital Converter (TDC), and note the difference of the round trip. In another embodiment, this could be n*clock+phase, and n can be found through another technique (Synchronization or clock counting, discuss later). The TDC can measure the clock fine phase difference, which is within one clock cycle.

For the synchronization module, the synchronization can be done through a dedicated package and/or IEEE1588. For example, an uplink/master can send the request with current timestamp (counter) to a downlink/slave, the slave responds in a fixed time delay, and the master detects the response and compare to the current timestamp. The difference detected by the master can be the fixed delay plus cable delay. In one embodiment, the package can be a MAC (Media Access Control) package over Ethernet. To further improve the stability, a pre-request package can be sent from uplink/ master to downlink/slave to clear all buffered data, and the downlink/slave responses back with acknowledge package after all buffers are cleared.

The direct detection of the sync package to count the clock cycles is necessary to determine the counting difference in addition to locking the master and slave nodes together using the master clock's oscillator frequency. The direct detection is to monitor the transmission and/or the receiving at lower level, instead of high level (such as UDP). This method can guarantee the package detected with minimum variance. In one embodiment, the detection can be implemented as detecting Start of Frame Delimiter (SFD) by the chip produced by Texas Instruments. If the sync package is used without the direct detection or the package travels through standard Ethernet switch, the overall time difference has multiple peaks which spreads more than one clock cycle, which is 8 nanoseconds nominal in Gigabit Ethernet, as disclosed in Gueorguiev (US 2012/0153166; see paragraph [0057]). Combining the clock counting and the clock phase monitoring, the overall difference below 1 nanosecond is achievable without multiple peak effect, namely the hardware-assisted direct detection method is necessary. And this method can be implemented with any dedicated package, including IEEE1588 package (PTPv1 and PTPv2).

As in PET, every detected event matters. The two types of events, prompt coincident events and random coincident events, are used together to reconstruct the final image. Every prompt coincident event with correct position information contributes to the signal, thus increases the signal-noise ratio, while every random coincident event contributes to the noise, thus decreases the signal-noise ratio. Any event, which should be in prompt, but being classified into random, because of the sync, will decrease the SNR, because the signal is wrongly classified as noise. On the other hand, any random event being wrongly classified into prompt, will also decrease the signal-noise ratio, because their position information is randomized.

The software-only package based method without direct detection cannot achieve good timing resolution, because of the multiple-peak effect. The multi-peak effect further decreases the signal-noise ratio, as it wrongly classifies some prompt coincident events into random coincident events and/or vice versa. Furthermore, the multi-peak effect forces user to choose bigger timing window in order not to lose prompt events and the bigger timing window increases the count rate of random events, thus decrease signal-noise ratio.

For data processing and storage, in a centralized system or software system, the coincidence processing unit (CPU) can send the information to all singles processing units (SPUs) and record the difference. In a distributed system, one SPU is chosen as the origin, all others can be synchronized to this SPU, and all difference can be either stored at uplink or downlink. It is noted that when the system power is on, this synchronization process can be done automatically without manual intervention.

In another aspect, the integrated interface can be implemented in other systems. For example, it can be used in a gamma camera system or gamma probe, especially a dynamic gamma camera or handheld gamma camera. In such a system, the data acquired is synchronized with the orientation information. The integrated interface can also be used in a SPECT system, where the rotation information can be synchronized.

While the phase detection method and correction can be done on either master or slave side, a master-slave configuration is needed to ensure all modules are synchronized, in either centralized or distributed CPU. In a centralized system configuration, for each connection, the uplink is the master and downlink is slave. In a distributed system, one node can have one or more connections, but the node can be slave on up to one connection. This will ensure the system has only one ultimate master node, from which the clock and synchronization originate.

DETAILED DESCRIPTION OF THE INVENTION

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

All publications mentioned are incorporated by reference for the purpose of describing and disclosing, for example, the designs and methodologies that are described in the publications that might be used in connection with the presently described invention. The publications listed or discussed above, below and throughout the text are provided solely for their disclosure prior to the filing date of the present application. Nothing herein is to be construed as an admission that the inventors are not entitled to antedate such disclosure by virtue of prior invention.

Figure 1:
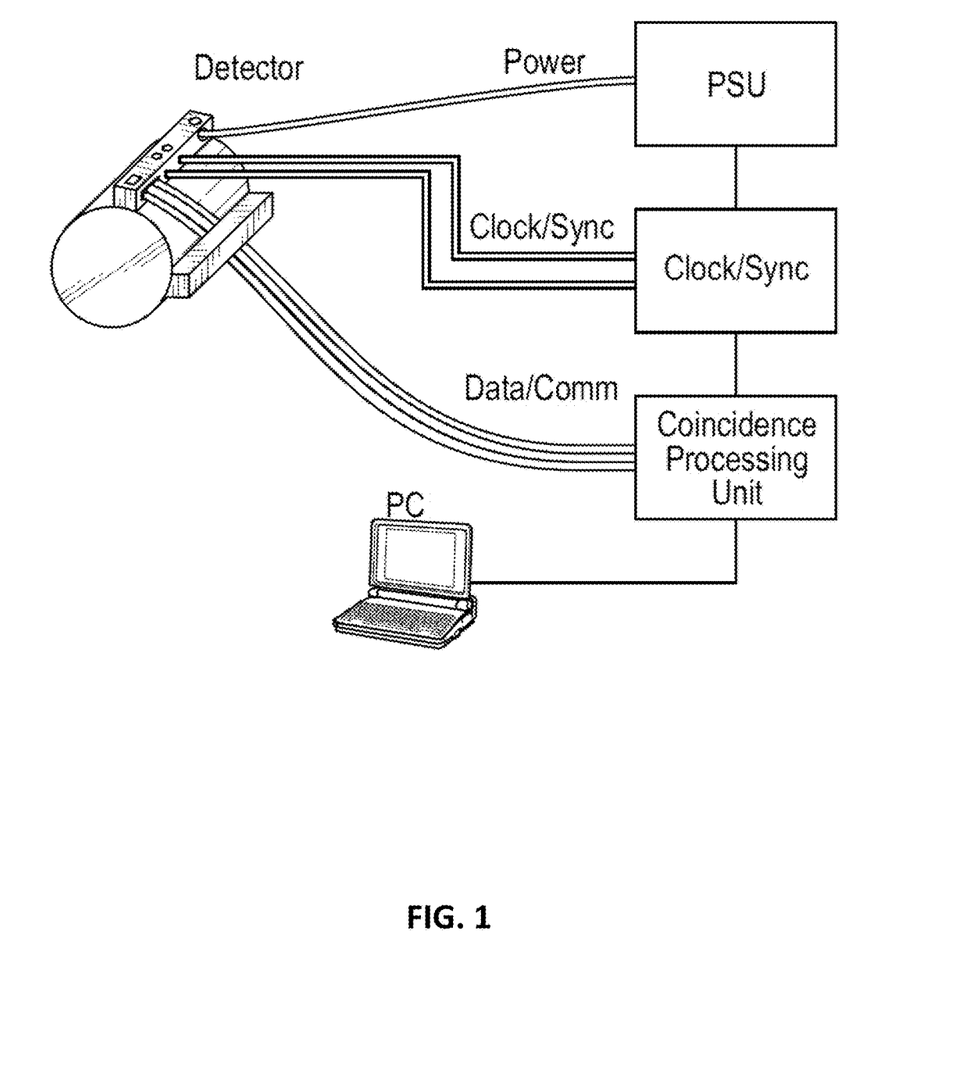
FIG. 1 is a schematic view of a conventional PET scanning device that includes detectors, power cable, clock cable, sync cable, data cable, coincidence processing unit and PC.

FIG. 1 illustrates a conventional Positron Emission Tomography (PET) that may include a power module, a clock/synchronization module, and a communication module. For example, Gigabit Ethernet, 10G Ethernet, Fast Ethernet (100M), 10M Ethernet or custom speed Ethernet based solution can be used in the communication module.

Figure 2:
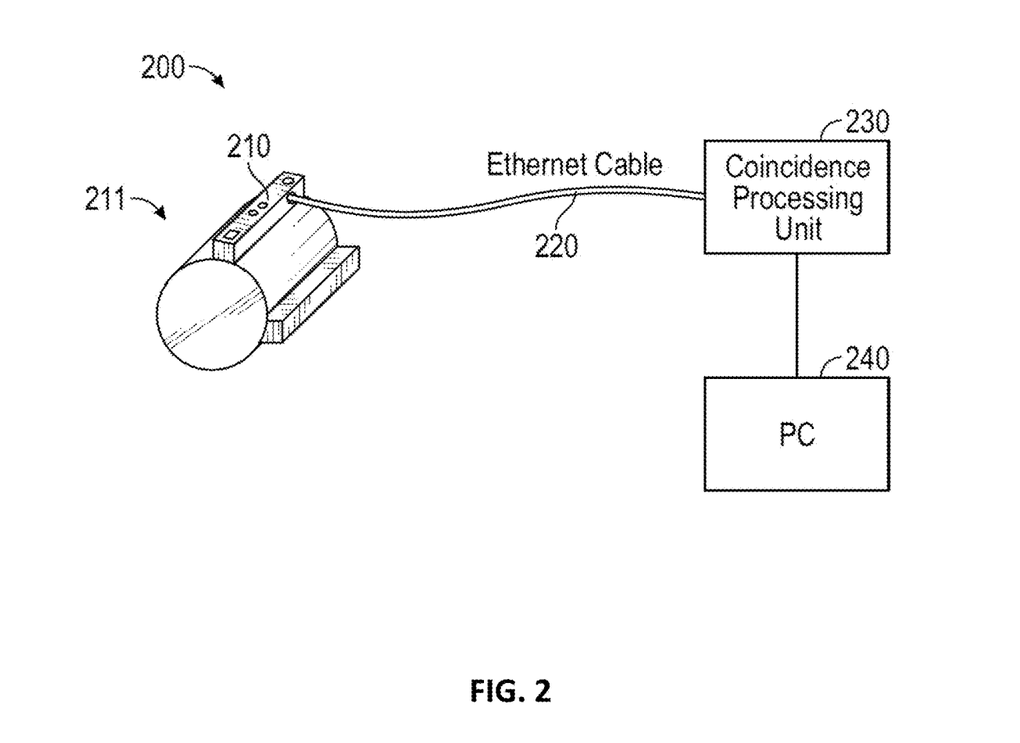
FIG. 2 is a schematic view of a structure including an Ethernet cable, coincidence processing unit, PC and detectors in the present invention.

Referring to FIG. 2, a Positron Emission Tomography (PET) device 200 may include a detector 210 having a power module 211, an Ethernet cable 220, and a coincidence processing unit (CPU) 230. In one embodiment, the power can be transmitted by a standard PoE (Power over Ethernet), which is configured to pass electric power along with data on twisted pair Ethernet cabling, and allows a single cable to provide both data connection and electric power to devices, for example from CPU 230 to detector 210. The PET device 200 may further include at least one PC 240 connected to CPU 230 to process the data received from the detector 210. A block diagram of Power over Ethernet (PoE) is shown in FIG. 3c, which may be used to transmit local power 310 to the detector 210 through the operation of a PoE Chip 320. In one embodiment, the Ethernet cable can be replaced by an HDMI cable.

It is noted that the power is delivered over the cable with a standard procedure to make sure the power delivery is safe. For example, only a small amount of power is configured to be delivered at the beginning.

Figure 3A:
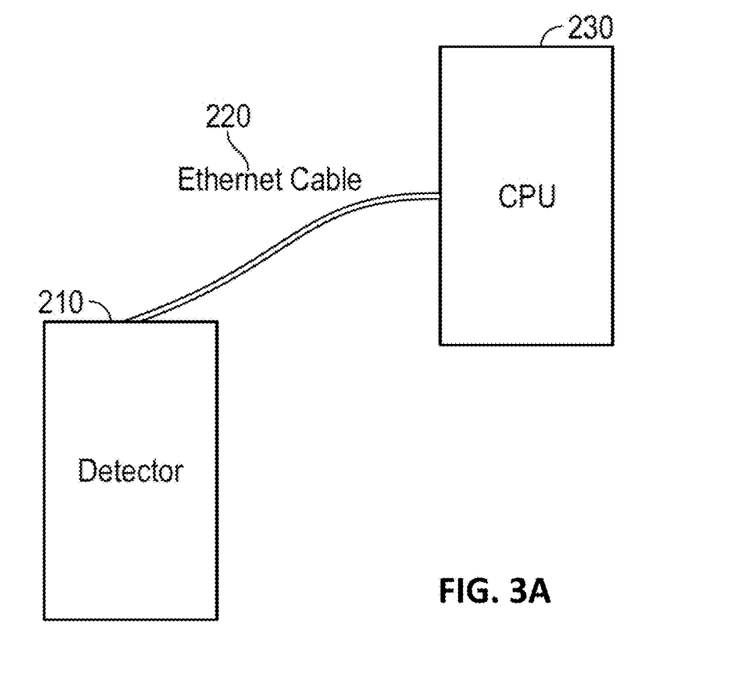
FIG. 3A is a schematic view of an interface (RJ45), including an Ethernet cable, coincidence processing unit and PC in the present invention.
Figure 3B:
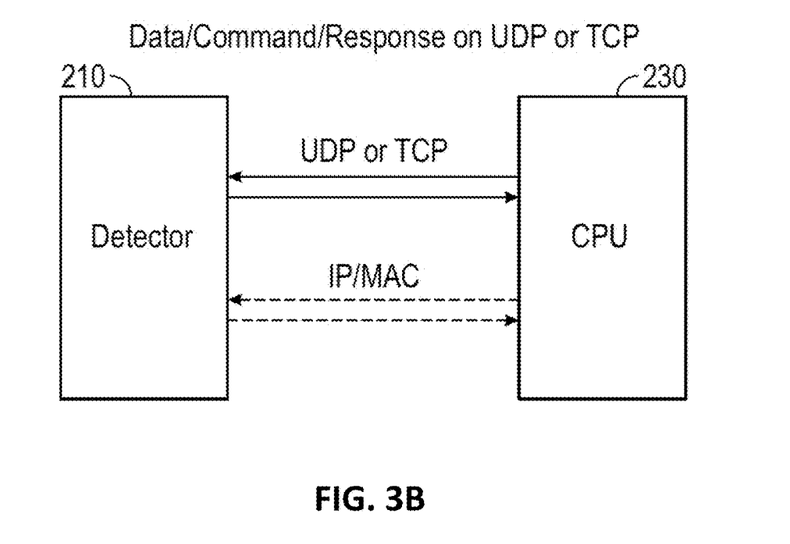
FIG. 3B is a schematic view of an Ethernet-based communication method in the present invention.
Figure 3C:
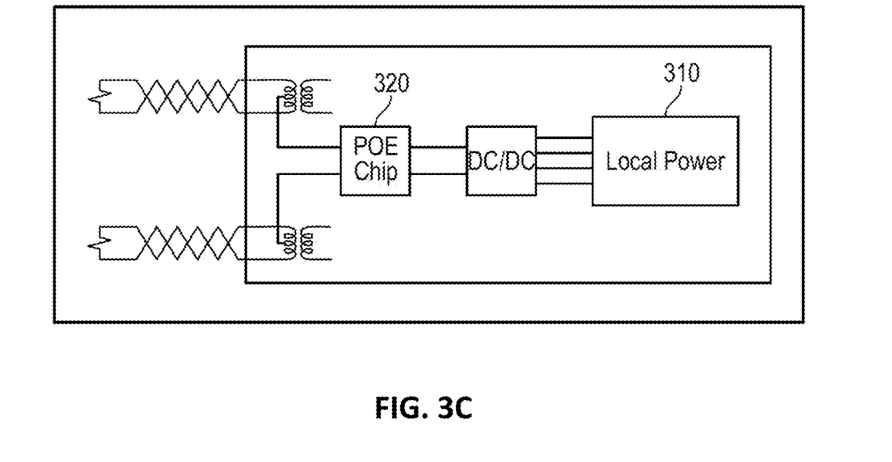
FIG. 3C is a schematic view of a power distribution over Ethernet in the present invention.

FIG. 3a shows a typical RJ 45 interface, which includes a detector 210, an Ethernet cable 220, and a coincidence processing unit (CPU) 230, while FIG. 3a shows a number of ways used for the detector 210 and the CPU 230 to communicate with each other. In one embodiment, the detector 210 and the CPU 230 can communicate through User Datagram Protocol (UDP), with which, computer applications can send data, command, etc. in this case referred to as datagrams, to other hosts on an Internet Protocol (IP) network. In another embodiment, the detector 210 and the CPU 230 can communicate through Transmission Control Protocol (TCP).

Figure 6:
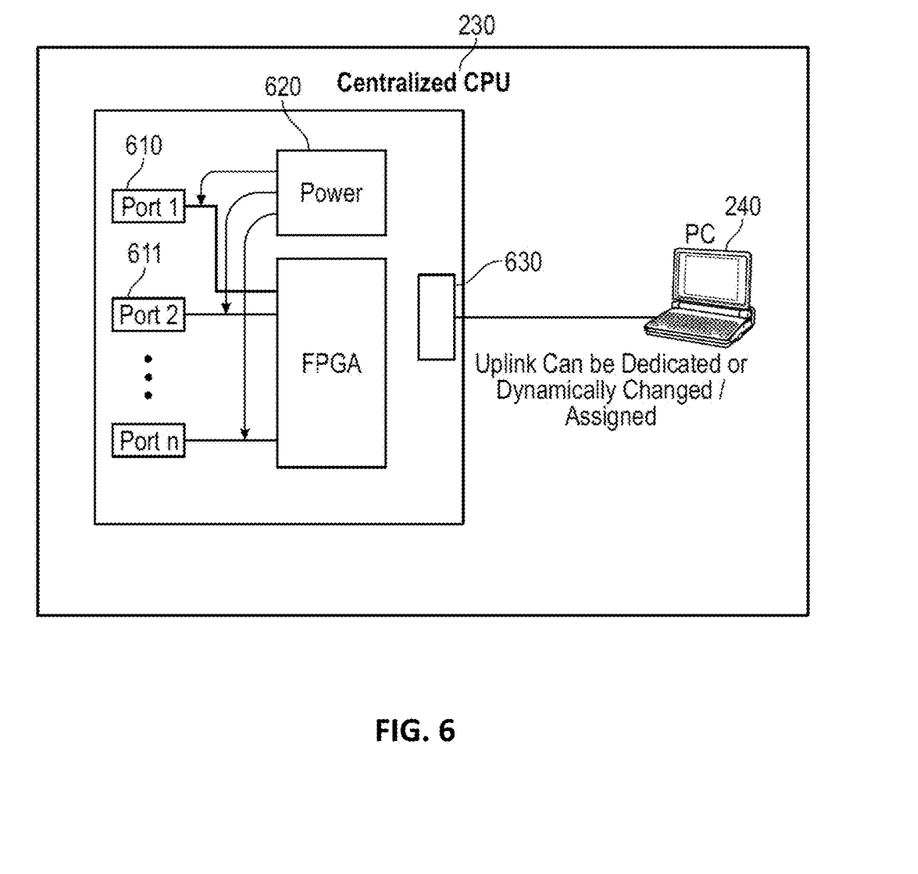
FIG. 6 is a schematic view of the coincidence processing unit that includes a plurality of RJ45 ports with power injectors, an output to PC and a power supply to all downstreams.

A block diagram of the CPU 230 is shown in FIG. 6, which may include a plurality of RJ 45 ports (610, 611 . . . ) with power injectors. A power supply 620 is provided for all downstream RJ 45 ports, and one output 630 to PC 240.

Figure 3D:
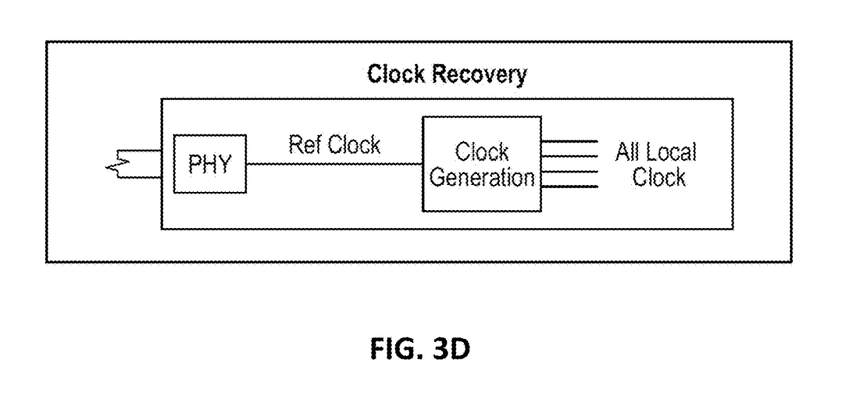
FIG. 3D is a schematic view of clock recovery in the present invention.
Figure 4:
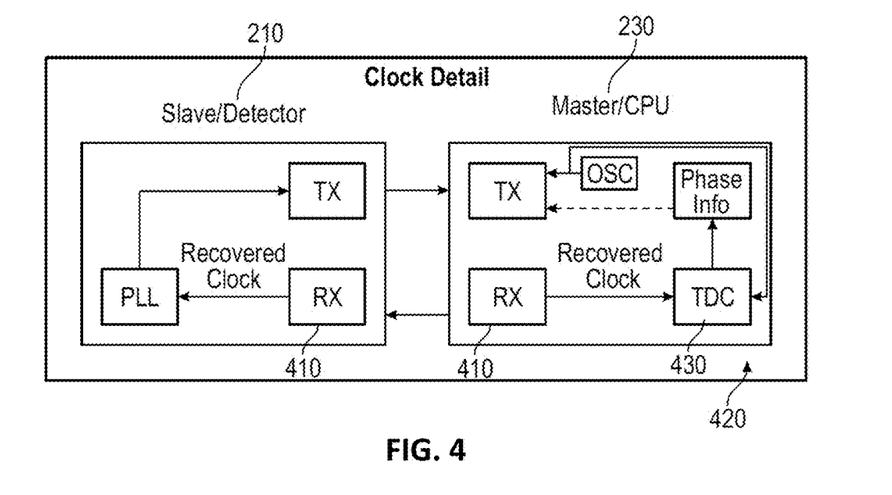
FIG. 4 is a schematic view of clock recovery in the present invention, where slave uses the recovered clock to transmit data and master detects the difference.

Referring to FIGS. 3d and 4 for the clock module, it is proved that the clock can be recovered from Ethernet. In one embodiment, the clock module has a recovery circuit (inside the receiver RX 410) to get the clock from the serial data, and the recovered clock is used to send the data back. A circuitry 420 on the coincidence processing unit 230 or uplink can be used to recover the clock from the detector module, monitor the difference with a Time to Digital Converter (TDC) 430, and note the difference of the round trip. In another embodiment, this could be n*clock+phase, and n can be found through another technique (Synchronization, discuss later).

Figure 5:
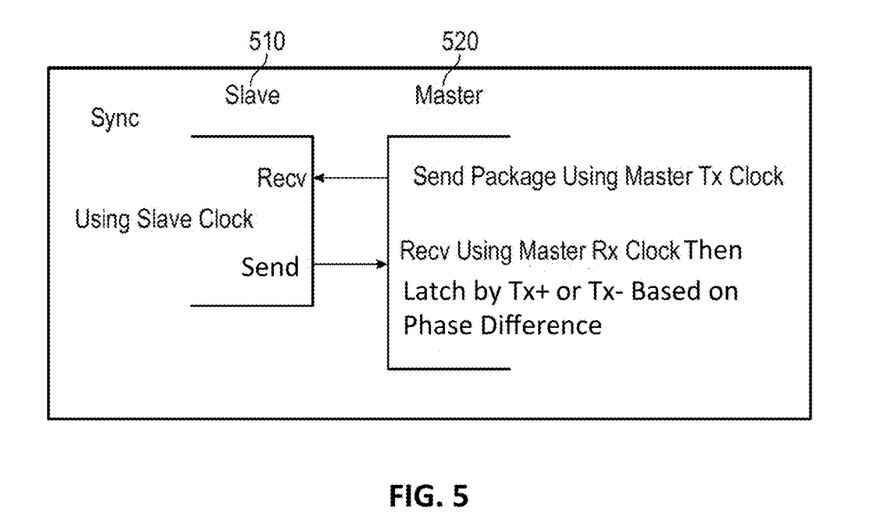
FIG. 5 is a schematic view of synchronization with a dedicated package implemented in the slave and master in the present invention.

In the synchronization module as shown in FIG. 5, in one embodiment, the synchronization can be done through a dedicated package and/or IEEE1588. For example, an uplink/master 520 can send the request with current timestamp (counter) to a downlink/slave 510, the slave responds in a fixed time delay, and the master detects the response and compare to the current timestamp. The difference detected by the master 520 can be the fixed delay plus cable delay. The cable delay can be parameter "n" described above. So, at the present stage, the system is synchronized with both clock phase and clock counting. In one embodiment, the package can be a UDP package over IP/MAC. To further improve the stability, a pre-request package can be sent from uplink/master 520 to downlink/slave 510 to clear all buffered data, and the downlink/slave 510 responses back with acknowledge package after all buffers are cleared.

Figure 7:
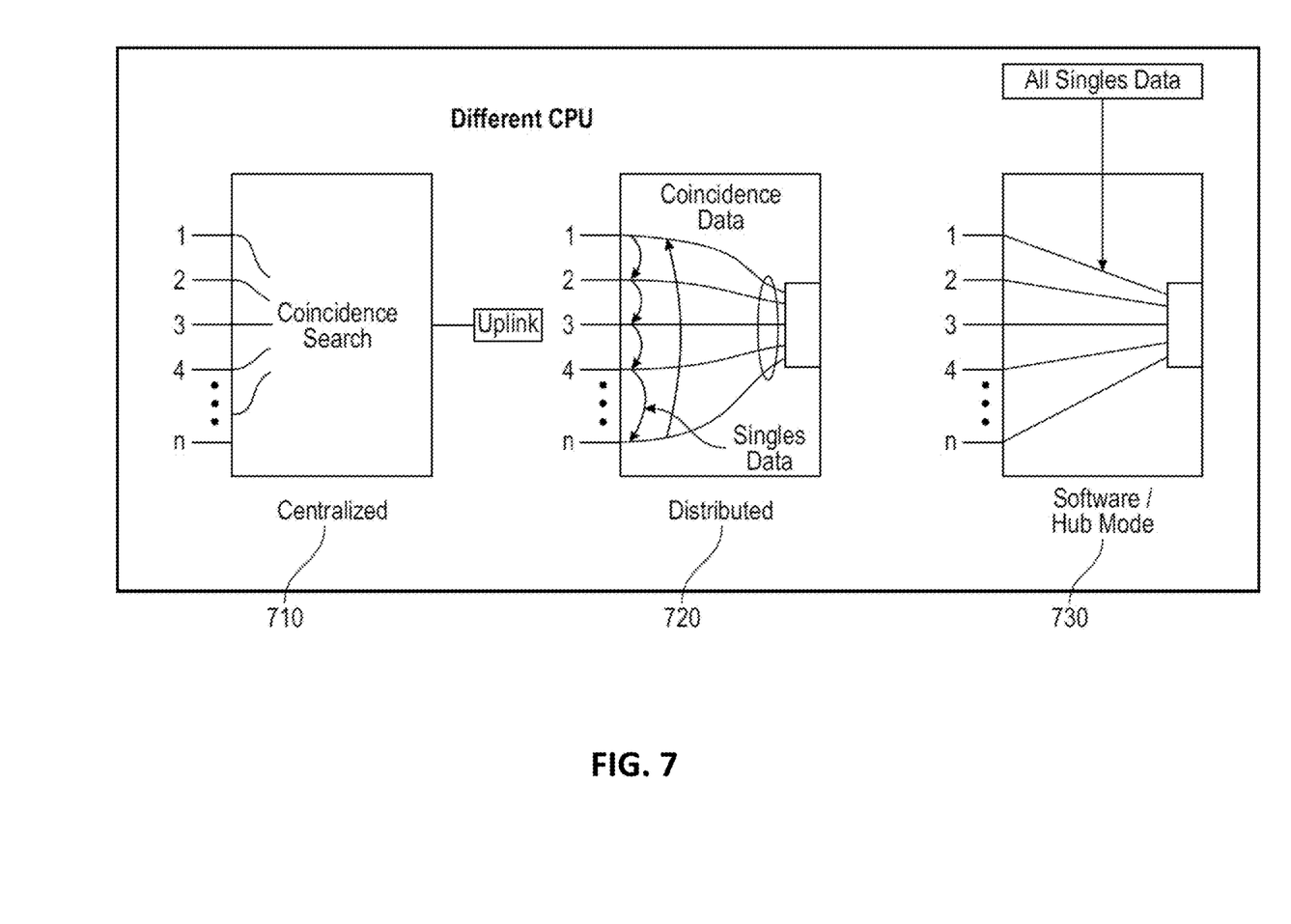
FIG. 7 is a schematic view of different CPUs in the present invention.

For data processing and storage as shown in FIG. 7, in a centralized system or software system, the coincidence processing unit (CPU) 710 can send the information to all singles processing units (SPUs) and record the difference. In another embodiment, the information can be kept at CPU. In a distributed coincidence processing unit (CPU) 720, one SPU is chosen as the origin, all others can be synchronized to this SPU, and all difference can be either stored at uplink or downlink. It is noted that when the system power is on, this synchronization process can be done automatically without manual intervention.

Figure 8:
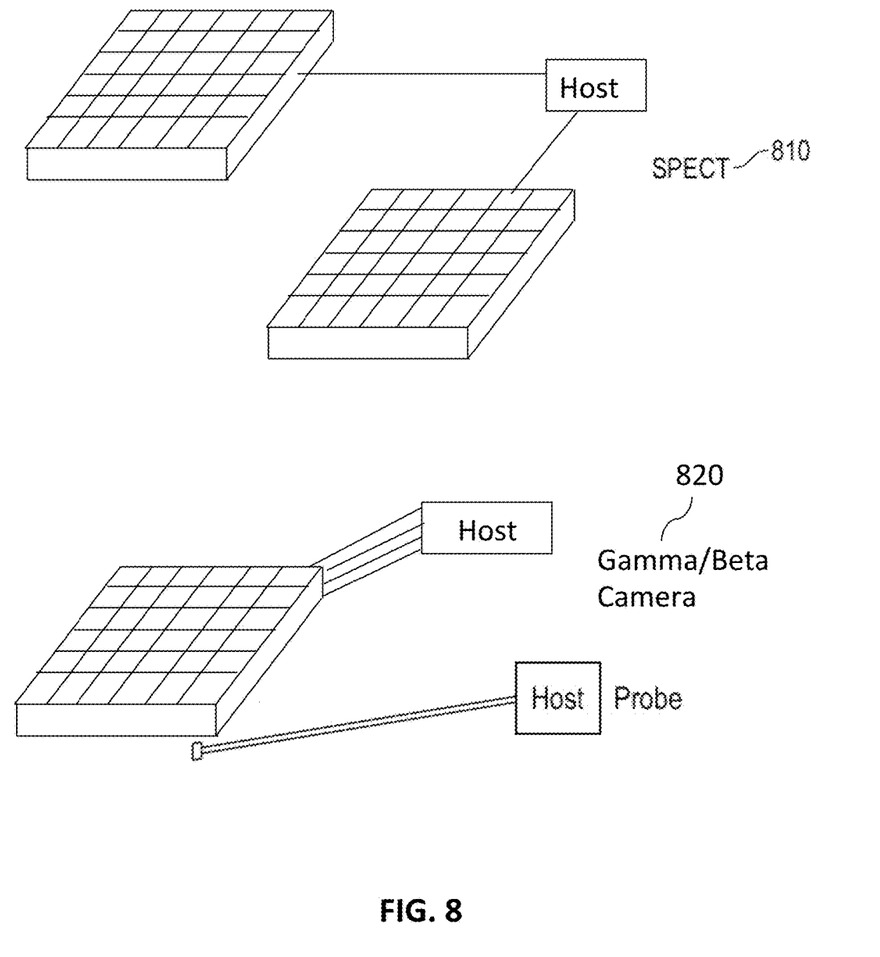
FIG. 8 is a schematic view of the implementation of the present invention in other systems.

In another aspect as shown in FIG. 8, the integrated interface can be implemented in other systems. For example, it can be used in a gamma camera system (or gamma probe) 820, especially a dynamic gamma camera or handheld gamma camera. In such a system, the data acquired is synchronized with the orientation information. The integrated interface can also be used in a SPECT system 810, where the rotation information can be synchronized. In another embodiment, the integrated interface can be used in a remotely located monitoring system 830.

Figure 9:
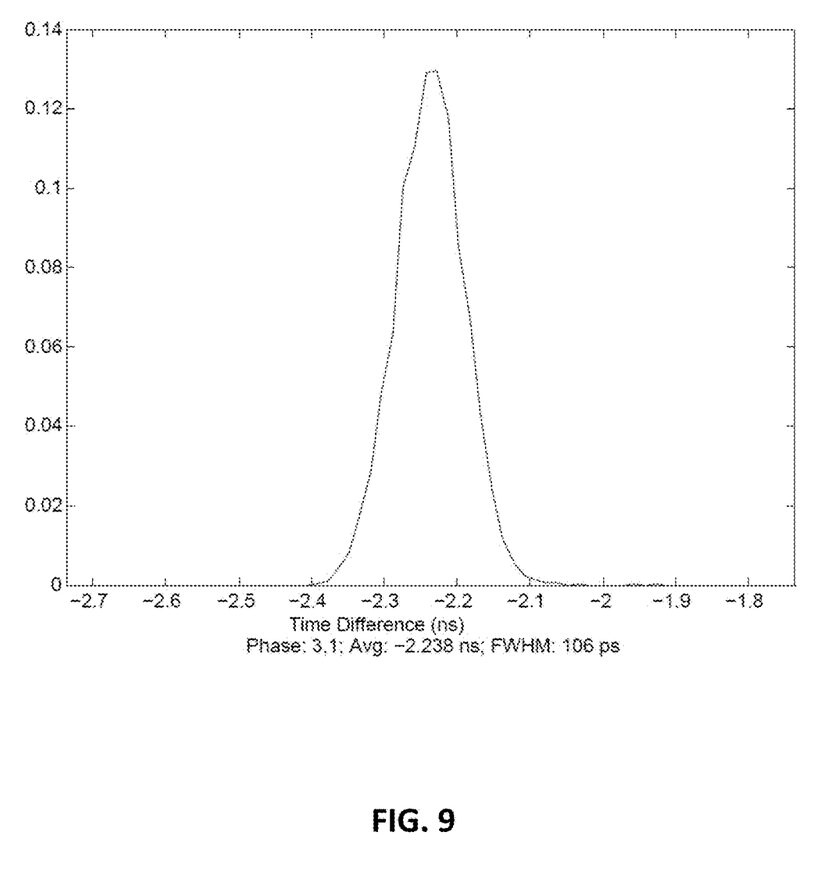
FIG. 9 is the test result of an experimental setup according to the present invention to eliminate multiple peak effect.

An experimental setup has been built to have one master node and two slave nodes. A test pulse signal is split into two and fed into the two slave nodes through two coaxial cables, one cable is about 40 cm longer than the other one. The pulse is repeated periodically for measurement. The two slave nodes use power from the master node through PoE and communicate with master node through the UDP protocol. SFD based hardware-assisted direct detection of sync package is implemented. After synchronization with the master node through a customized package, each slave node detects the rising edge of the test pulse, records the timestamp and sends to the master node. The master node collects both time stamps, applies offset correction and sends to the PC, which calculates the difference of the timestamps for each pulse event and plots the count statistics as shown in FIG. 9. The result shows only one peak and Full-Width-Half-Maximum (FWHM) resolution is 106 picoseconds.

Having described the invention by the description and illustrations above, it should be understood that these are exemplary of the invention and are not to be considered as limiting. Accordingly, the invention is not to be considered as limited by the foregoing description, but includes any equivalents.

What is claimed is:

1. A Positron Emission Tomography (PET) device comprising:
    one or more scan detectors configured to detect radiation emitted from a patient's body placed within said PET device;
    at least one coincidence processing unit (CPU) to receive data from said detectors; and
    an Ethernet interface to communicate between at least one CPU and said detector,
    wherein the detector is configured to transmit data, receive power, recover clock and synchronize information between the detector and the CPU through the Ethernet interface,
    wherein the PET device has a clock module having a clock recovery circuitry on the detector to recover the clock from CPU, and on the CPU to recover the clock from the detector, monitor the fine difference with a Time to Digital Converter (TDC); and a synchronization module to count clock cycles to determine the coarse difference, and a direct detection of synchronization package used on master and/or slave sides to eliminate multiple peak effect.

2. The PET device of claim 1, further comprising a hub configuration including a customized hub having at least one upstream port and multiple downstream ports performing the clock and synchronization functions. The hub can be placed between a CPU (or another hub) and one or more detectors (or hubs).

3. The PET device of claim 1, wherein the Ethernet interface includes Gigabit Ethernet, 10G Ethernet, Fast Ethernet (100M), 10M Ethernet, or Ethernet at custom speed.

4. The PET device of claim 1 further comprising at least a personal computer (PC) connected to the CPU.

5. The PET device of claim 1, wherein the data transmission between the detector and CPU is through User Datagram Protocol (UDP), Transmission Control Protocol (TCP), or Internet Protocol (IP).

6. The PET device of claim 1, wherein a dedicated package and/or IEEE1588 is used to implement the synchronization between the detector and CPU.

7. The PET device of claim 1, wherein the CPU is a centralized CPU, a distributed CPU or a software CPU.

8. The PET device of claim 1, wherein the Ethernet interface can be used in other image systems, including SPECT, Gamma Camera and Gamma Probe.

9. The PET device of claim 1, wherein an Ethernet cable is used for the Ethernet interface.

10. The PET device of claim 1, wherein an HDMI cable is used for the Ethernet interface.

11. The PET device of claim 2, wherein the hub configuration is placed between a CPU and one or more detectors.

12. The PET device of claim 2, wherein the hub configuration is placed between hubs.

\* \* \* \* \*